US008313070B2

(12) United States Patent
Kronner et al.

(10) Patent No.: US 8,313,070 B2
(45) Date of Patent: Nov. 20, 2012

(54) BASE-CLAMP ASSEMBLY

(76) Inventors: Richard F. Kronner, Roseburg, OR (US); David D. Kronner, Roseburg, OR (US)

( * ) Notice: Subject to any disclaimer, the term of this patent is extended or adjusted under 35 U.S.C. 154(b) by 426 days.

(21) Appl. No.: 12/582,605

(22) Filed: Oct. 20, 2009

(65) Prior Publication Data

US 2010/0108841 A1 May 6, 2010

Related U.S. Application Data

(60) Provisional application No. 61/110,069, filed on Oct. 31, 2008.

(51) Int. Cl.
*A47B 96/06* (2006.01)

(52) U.S. Cl. ................. 248/231.51; 248/214; 248/286.1

(58) Field of Classification Search ............. 248/229.13, 248/229.1, 231.51, 231.61, 316.6, 316.8; 600/102, 228, 229
See application file for complete search history.

(56) References Cited

U.S. PATENT DOCUMENTS

| | | | | | |
|---|---|---|---|---|---|
| 114,243 | A | | 4/1871 | Wood et al. | |
| 373,362 | A | | 11/1887 | Hamilton | |
| 837,642 | A | * | 12/1906 | Powell | 248/95 |
| 1,084,427 | A | | 1/1914 | Hanks | |
| 1,403,863 | A | | 1/1922 | Peat | |
| 4,018,412 | A | * | 4/1977 | Kees et al. | 248/214 |
| 4,142,632 | A | | 3/1979 | Sandel | |
| 4,170,336 | A | | 10/1979 | Malis | |
| D263,076 | S | | 2/1982 | Sandel | |
| D263,745 | S | | 4/1982 | Sandel | |
| 4,355,631 | A | | 10/1982 | LeVahn | |
| 4,417,710 | A | | 11/1983 | Adair | |
| D275,229 | S | | 8/1984 | Sanderson et al. | |
| 4,573,452 | A | | 3/1986 | Greenberg | |
| 4,596,329 | A | | 6/1986 | Eldridge, Jr. | |
| 4,597,493 | A | | 7/1986 | Bruso | |
| 4,617,916 | A | | 10/1986 | LeVahn et al. | |
| 4,796,846 | A | * | 1/1989 | Meier et al. | 248/286.1 |
| 4,863,133 | A | | 9/1989 | Bonnell | |
| 4,867,404 | A | | 9/1989 | Harrington et al. | |
| D306,481 | S | | 3/1990 | Lang | |
| 5,082,111 | A | | 1/1992 | Corbitt, Jr. et al. | |
| 5,104,103 | A | | 4/1992 | Auchinleck et al. | |
| 5,186,174 | A | | 2/1993 | Schlondorff et al. | |
| 5,205,522 | A | | 4/1993 | Nakamura | |
| 5,224,680 | A | | 7/1993 | Greenstein et al. | |
| 5,284,130 | A | | 2/1994 | Ratliff | |
| 5,380,338 | A | | 1/1995 | Christian | |

(Continued)

OTHER PUBLICATIONS

Stoney, Ronald J., M.D.; "How to Achieve Optimum Exposure of the Upper Abdominal Aorta and Its Branches"; Minnesota Scientific Inc.; Dec. 1986; 4 pages.

(Continued)

*Primary Examiner* — Gwendolyn W Baxter
(74) *Attorney, Agent, or Firm* — Kolisch Hartwell, P.C.

(57) ABSTRACT

A base-clamp assembly for supporting an instrument relative to a patient position adjacent to an instrument-support rail. The base-clamp assembly may comprise a base, a rail clamp, and an actuator assembly. The rail clamp may attach the base to the rail. A shank clamp may attach a shank to the base. The actuator assembly may be operable for opening and/or closing the rail clamp. A drive assembly may provide for moving a force-applying element relative to the base and a movable rail jaw for closing the rail clamp. The drive assembly may also be operable for opening and closing the shank clamp.

2 Claims, 5 Drawing Sheets

U.S. PATENT DOCUMENTS

| | | | | |
|---|---|---|---|---|
| 5,383,637 | A | 1/1995 | Biber | |
| D358,642 | S | 5/1995 | Michelson | |
| 5,441,042 | A | 8/1995 | Putman | |
| 5,494,034 | A | 2/1996 | Schlondorff et al. | |
| 5,513,827 | A | 5/1996 | Michelson | |
| 5,558,622 | A | 9/1996 | Greenberg | |
| 5,571,072 | A | 11/1996 | Kronner | |
| 5,649,946 | A | 7/1997 | Bramlet | |
| 5,662,300 | A | 9/1997 | Michelson | |
| 5,681,325 | A | 10/1997 | Hasson | |
| 5,785,643 | A | 7/1998 | Lynn | |
| 5,810,712 | A | 9/1998 | Dunn | |
| 5,810,864 | A | 9/1998 | Schaller | |
| 5,824,007 | A | 10/1998 | Faraz et al. | |
| 5,836,453 | A | 11/1998 | Herrera | |
| 5,876,325 | A | 3/1999 | Mizuno et al. | |
| 5,907,664 | A | 5/1999 | Wang et al. | |
| 5,918,844 | A | 7/1999 | Ognier | |
| 5,957,423 | A | 9/1999 | Kronner | |
| 6,080,181 | A | 6/2000 | Jensen et al. | |
| 6,200,263 | B1 | 3/2001 | Person | |
| 6,213,671 | B1 | 4/2001 | Chang | |
| 6,413,264 | B1 | 7/2002 | Jensen et al. | |
| 6,461,372 | B1 | 10/2002 | Jensen et al. | |
| 6,540,739 | B2 | 4/2003 | Lechot | |
| 6,575,298 | B1 | 6/2003 | McArthur et al. | |
| 6,610,009 | B2 | 8/2003 | Person | |
| 6,613,039 | B1 | 9/2003 | Namba | |
| 6,622,980 | B2 * | 9/2003 | Boucher et al. | 248/231.51 |
| 6,632,170 | B1 | 10/2003 | Bohanan et al. | |
| 6,716,163 | B2 | 4/2004 | Muhanna et al. | |
| 6,966,876 | B2 | 11/2005 | Irion et al. | |
| 6,969,192 | B1 | 11/2005 | Hollowell | |
| 6,971,617 | B2 * | 12/2005 | Nguyen | 248/286.1 |
| 7,179,225 | B2 | 2/2007 | Shluzas et al. | |
| 7,670,281 | B2 | 3/2010 | Kronner | |
| 2006/0079864 | A1 | 4/2006 | Kronner | |
| 2010/0114117 | A1 | 5/2010 | Kronner | |

OTHER PUBLICATIONS

Computer Motion, Inc. (Goleta, CA); "Enhancing Performance Through Robotics" and "Robotic Enhancement Technology"; no date; 2 pages.

Leonard Medical, Inc. (Huntingdon Valley, PA); literature on The Leonard Arm, Leonard Arm Jr., Laparoscope Holder and Instrument Holder; Oct. 20, 1993; 11 pages.

Allen Medical Systems; "Leonard Arm Scope & Retractor Holders"; copyright 1996 Allen Medical Systems; 7 pages.

Omni-Tract Surgical a Division of Minnesota Scientific (St. Paul, MN); literature on the Omni-Tract Corral Retractor, Pittman IMA Retractor System, Omni-LapoTract Support Systems, and Omni-Tract Accessories; 1991 and 1993; 8 pages.

Omni-Tract Surgical (St. Paul, MN); "Omni-Lapo Tract Scope and Instrument Holder"; copyright 2006 Omni-Tract Surgical; 2 pages.

Computer Motion, Inc. (Goleta, CA); "AESOP: Automated Endoscope System for Optimum Positioning"; no date; 4 pages.

Computer Motion, Inc. (Goleta, CA); literature on AESOP Automated Endoscope System for Optimum Positioning; Fall 1997; 5 pages.

Cuschieri, Alfred, M.D.; "Minimum Access Surgery and the Future of Interventional Laparoscopy"; The American Journal of Surgery vol. 161; Mar. 1991; 4 pages.

Omni-Tract Surgical (St. Paul, MN); catalog featuring surgical components, retractors, blades, and accessories; copyright 1991 Omni-Tract Surgical; 8 pages.

NASA Tech Briefs; "Robotics for Safer Surgery"; NASA Tech Briefs vol. 18, No. 1, pp. 16-18; Jan. 1994; 3 pages.

Nathanson, L.K., et al; "Laparoscopic Cholecystectomy"; Br. J. Surg. 1991 vol. 78, No. 2, pp. 155-159; copyright 1991 Butterworth-Heinemann Ltd.; 5 pages.

Omni-Tract Surgical (St. Paul, MN); literature on the Stoney Mini Vascular Retractor System—VM100; copyright 1991 Omni-Tract Surgical; 4 pages.

Omni-Tract Surgical (St. Paul, MN); literature on the FastSystem Stoney Peripheral Vascular Retractor System—VF100; no date; 2 pages.

Unknown; The Iron Intern Robotic Retractor—Your Most Dependable Assistant; no date; 2 pages.

Berci, George, et al; "New Ideas and Improved Instrumentation for Laparoscopic Cholecystectomy"; Surgical Endoscopy 1991 vol. 5 pp. 1 and 3; copyright 1991 Springer-Verlag; 2 pages.

Elmed, Inc. (Addison, IL); literature on the Elmed Endoscopic Fixation Device; 4 pages, 1992.

World of Medicine Lemke GmbH; 510(K) Summary SightFix, stamped Mar. 18, 2003; 2 pages.

Jaspers, Joris E. et al.; abstract of "Camera and Instrument Holders and Their Clinical Value in Minimally Invasive Surgery", Surgical Laparoscopy Endoscopy & Percutaneous Techniques, vol. 14(3) Jun. 2004; Lippincott Williams & Wilkins; 1 page.

Richard M. Kronner, M.D.; "Letter to Peter Sabido of Kolisch Hartwell"; Jan. 17, 2006; 2 pages.

Thompson Surgical Instruments, Inc; "Thompson Scope Holder"; downloaded from http://www.thompsonsurgical.com on Feb. 17, 2006; 1 page.

Thompson Surgical Instruments, Inc; "Flexbar/Thompson Scope Holder"; downloaded from http://www.thompsonsurgical.com on Feb. 17, 2006; 1 page.

UCI Medical Center (University of California, Irvine); "Smooth Operator: The Surgical Robot"; downloaded from www.ucihealth.com on Feb. 21, 2006; 2 pages.

Armstrong Healthcare Limited; "EndoAssist: The Camera Manipulator for Laparoscopic Surgery"; no date; 1 page.

MEDIAFLEX; Advertisement titled "Surgical Devices Since 1969"; no date; 1 page.

A Gray Lerner, M.S., et al; "A Passive Positioning and Supporting Device for Surgical Robots and Instrumentation"; no date; 11 pages.

* cited by examiner

BASE-CLAMP ASSEMBLY

RELATED APPLICATION

This application claims the benefit of U.S. Provisional Application No. 61/110,069, filed Oct. 31, 2008, which application is incorporated herein by reference in its entirety for all purposes.

BACKGROUND

Laparoscopic surgery is a procedure in which surgical instruments and a viewing scope, referred to generally as an endoscope and more specifically as a laparoscope, are inserted through small puncture wounds or incisions into the abdominal cavity of a patient. A small video camera is attached to the laparoscope and connected to a television monitor for viewing the procedure. The instruments and the laparoscope may be inserted through cannulae, which are first inserted through the incisions. The cannulae allow the instruments and the scope to be removed and reinserted as necessary. The viewing laparoscope may be inserted through a cannula, which is usually inserted through an incision made in the umbilicus. The scope is then directed towards the pelvis for pelvic surgery or towards the liver for gallbladder surgery.

Instrument-supporting apparatuses have been developed that support such surgical instruments or viewing scopes. Examples of such apparatuses are illustrated in U.S. Pat. No. 5,957,423 and U.S. Patent Application Publication Number 2006/0079864. The instrument-supporting apparatuses must be securely fastened to the frame of the surgical support, which frame may be some form of rail that extends along a side of a surgical platform. It is desirable to have a rail grip, also referred to as a base-clamp assembly that may be rapidly and easily secured to or removed from the rail.

BRIEF SUMMARY

A base-clamp assembly may be used for supporting an instrument-support apparatus having a shank extending adjacent to an equipment-mounting rail for supporting instruments relative to a patient position adjacent to the rail. The base-clamp assembly may comprise a base, a rail clamp, and an actuator assembly. A shank clamp may attach a shank to the base. The rail clamp may have a first rail jaw fixedly supported relative to the base, and a second rail jaw mounted for pivoting relative to the base opposing and movable relative to the first rail jaw. The first and second rail jaws may form a rail opening. The second rail jaw may be movable between an open position in which the rail opening is sized for receiving a rail and a closed position in which the rail jaws securely hold the rail. The actuator assembly may be operable for moving the second rail jaw relative to the first rail jaw. The actuator assembly may include a first force-applying element movable relative to the base and the second rail jaw for applying a first force to the second rail jaw tending to move the second rail jaw toward the closed position. A drive assembly may be manipulable for moving the first force-applying element relative to the base.

DETAILED DESCRIPTION

Figure 1:
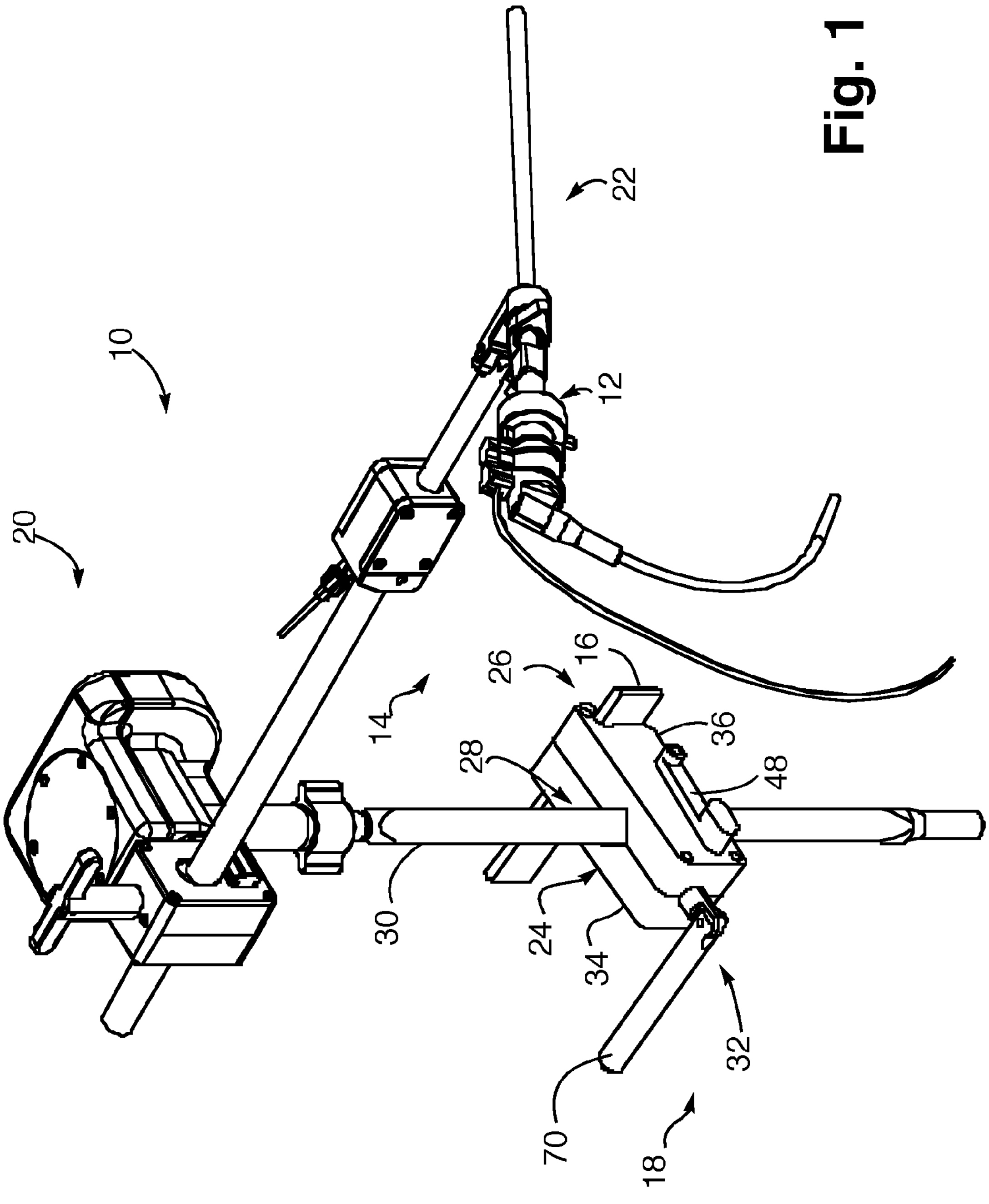
FIG. 1 is an isometric view of an example of an instrument-support apparatus.
Figure 2:
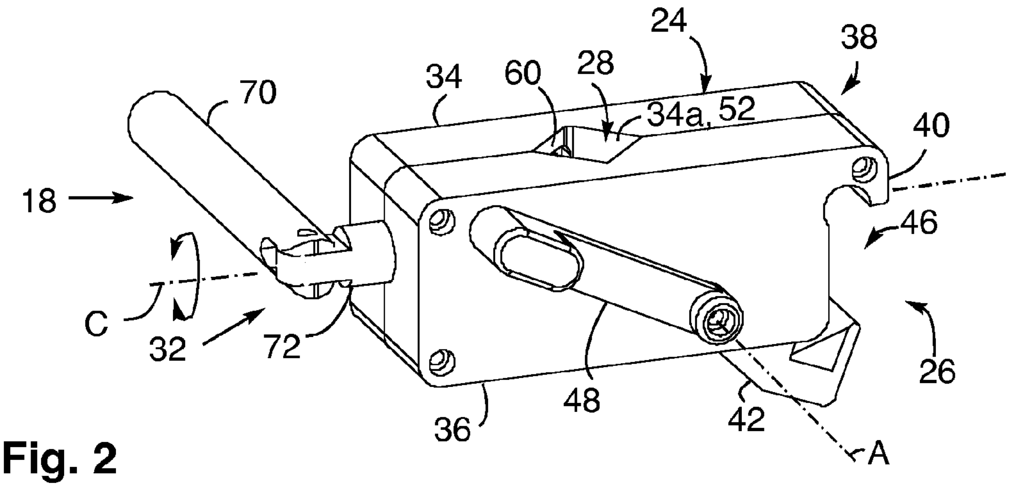
FIG. 2 is an isometric view of an example of a base-clamp assembly that may be used in the instrument-support apparatus of FIG. 1
Figure 3:
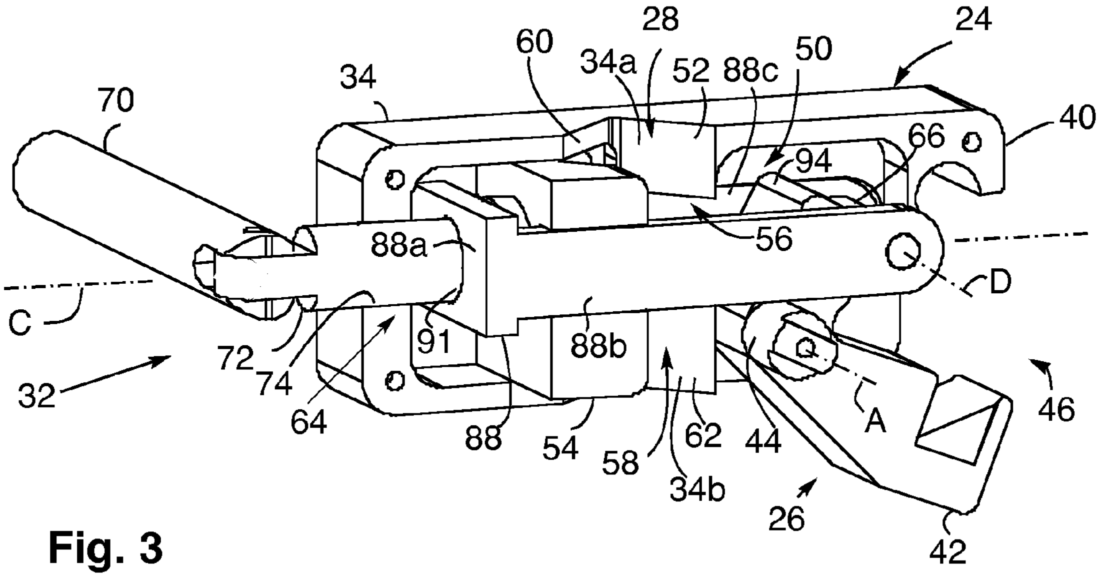
FIG. 3 is an isometric view of the base-clamp assembly of FIG. 2 with a near housing section and side handle removed.
Figure 4:
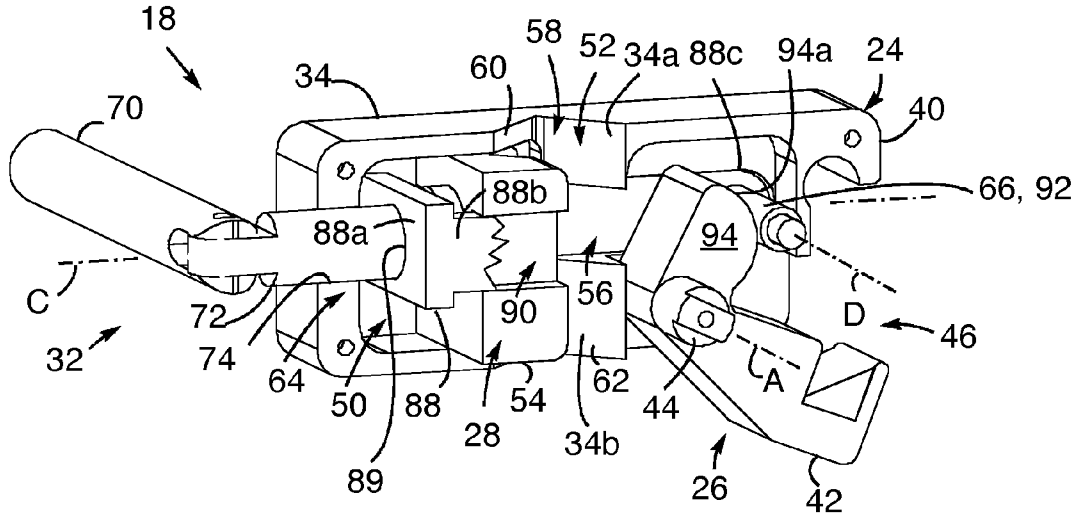
FIG. 4 is a partial fragmentary isometric view of an example of a base clamp assembly similar to FIG. 3 but with a portion of a pulling component removed.

FIG. 1 depicts an example of an instrument-support apparatus 10. The instrument support apparatus may support any appropriate instrument 12, such as an endoscope, relative to an operating table (not shown) defining a patient position 14. The operating table may have an external frame, such as a rail 16, for supporting equipment for use in surgery. The instrument may be inserted into a cannula (not shown), which includes any suitable structure configured to allow instruments to be inserted into and removed from the patient as necessary.

Instrument support apparatus 10 may include a base-clamp assembly 18, a motion assembly 20, and a support assembly 22, as shown in FIG. 1. Base-clamp assembly 18 may include any suitable structure configured to secure the instrument-support apparatus to rail 16. As shown more particularly in FIGS. 2-9, the base-clamp assembly may include a base 24, a rail clamp 26, a shank clamp 28 for supporting a shank 30 supporting in turn the balance of instrument support apparatus 10, and an actuator assembly 32. Base 24 may be any suitable frame for supporting shank 30 relative to rail 16. In this example, base 24 is formed of first and second housing sections 34 and 36. Housing sections 34 and 36 may be attached by screws or other suitable fasteners to form a housing 38 generally covering internal mechanisms associated with base-clamp assembly 18, as shown.

Although base-clamp assembly 18 is shown to be mounted on a horizontal rail 16, the base-clamp assembly may be configured to be mounted in any suitable orientation, and rail 16 may be any suitable frame element. Although not required, the illustrated example of base-clamp assembly 18 is dual-acting in the sense that it provides clamping of base 24 onto rail 16 and also secures shank 30 to the base, and thereby to the rail. Rail clamp 26 may selectively secure base 24 to rail 16. Rail clamp 26 may include a fixed rail jaw 40 that may be fixedly supported relative to base 24, and a movable rail jaw 42 mounted for pivoting about a rail-jaw pivot axis A relative to the base.

Figure 5:
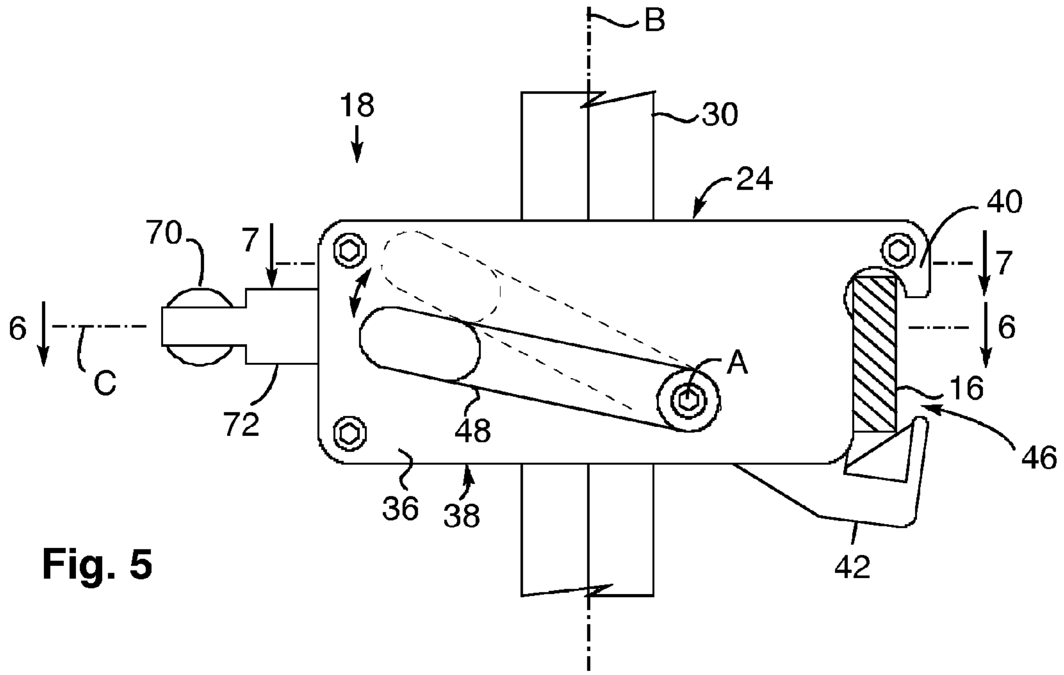
FIG. 5 a side view of the base-clamp assembly of FIG. 2 mounted onto a horizontal rail and vertical instrument-support shank.
Figure 6:
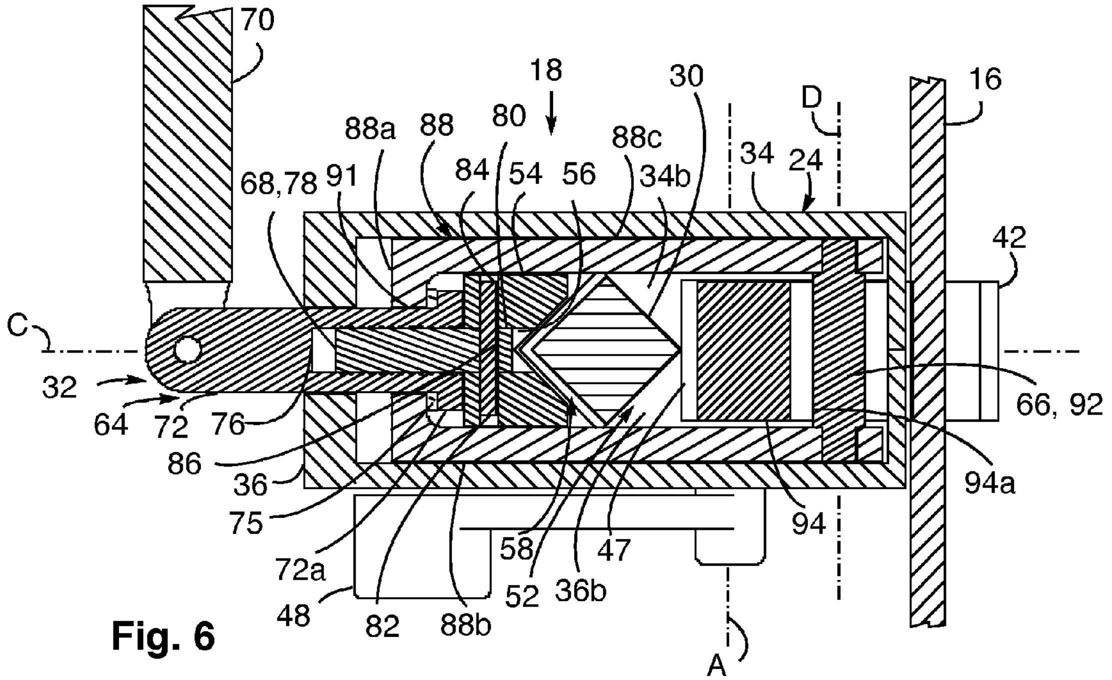
FIG. 6 is a cross section taken along line 6-6 in FIG. 5 with the base removed.

Rail jaw 42 may be mounted on an axle 44 that is pivotingly mounted to base 24 for pivoting about pivot axis A. Rail jaw 42 may oppose and be movable relative to rail jaw 40, and thereby relative to base 24, with the fixed and movable rail jaws forming a rail opening 46 between them. In this example, rail jaw 42 may be freely pivotable relative to base 24, and there may be a space or gap 47 between rail jaw 42 and the portion of base 24 adjacent to the fixed shank jaw 52, as shown in FIG. 6. The movable rail jaw may be movable between an open position in which the rail opening is sized for receiving a rail, as shown in FIGS. 2-4 and 8, and a closed position in which the rail jaws securely hold the rail, as shown in FIGS. 5 and 9. Rail jaw 40 may be formed in two sections as portions of housing sections 34 and 36, with each portion formed as a single piece of material with the respective housing section. Rail jaw 42 may be moved manually about pivot axis A by a release handle 48 attached to axle 44 and positioned outside of housing section 36, as shown particularly in FIG. 2.

Figure 7:
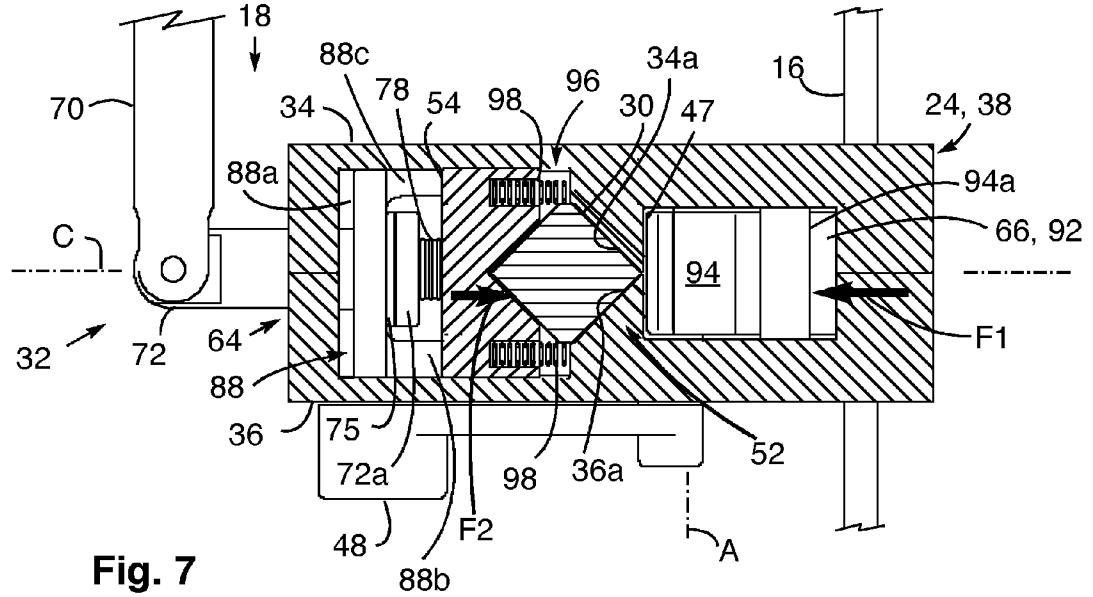
FIG. 7 is a cross section taken along line 7-7 in FIG. 5.

Base 24 defines an internal chamber 50. Shank clamp 28 includes opposing shank jaws 52 and 54. Shank jaw 52 may be fixedly supported relative to base 24 and shank jaw 54 may be mounted for movement toward and away from shank jaw 52. In this example, the surfaces of shank jaws 52 and 54 are beveled to mate with corresponding faces of shank 52, as shown in FIG. 7. Fixed shank jaw 52 may be formed in two portions of each of housing sections 34 and 36, with each portion formed as a single piece of material with the respective housing section. For example, housing section 34 may be formed of an upper shank-jaw portion 34*a* and a lower shank-jaw portion 34*b*. Similarly, housing section 36 may be formed of an upper shank-jaw portion 36*a* and a lower shank-jaw portion 36*b* that form fixed shank jaw 52 in combination with portions 34*a* and 34*b*.

The upper and lower shank-jaw portions are spaced apart with a channel 56 extending between them. Shank jaws 52 and 54 define a shank opening 58 extending along a shank axis B through which shank 30 extends in use. Base 24 includes upper keyway 60 and lower keyway 62 that align with opening 58 to accommodate passage of the shank. Movable shank jaw 54 is movable between an open position sized to freely receive shank 30, as shown in FIG. 6, and a closed position in which shank 30 is securely clamped during use, as shown in FIG. 7. The openings in the base are sized sufficiently large to accommodate the corresponding migration of shank 30 in base 24 during tightening of the base clamp assembly.

Actuator assembly 32 may provide manual manipulation of rail clamp 26 and/or shank clamp 28. The actuator assembly may include a drive assembly 64, a first force-applying element 66, and a second force-applying element 68. As shown in FIG. 7, the first force-applying element may be movable relative to base 24 and rail jaw 42 for applying a first force F1 to rail jaw 42 tending to close rail jaw 42. The second force-applying element may be for applying a second force F2 to shank jaw 54 tending to move shank jaw 54 between the open and closed positions.

Drive assembly 64 may include a handle 70 pivotingly attached at one end to a shaft 72 extending along a shaft axis C through an aperture 74 in the end of base 24. Shaft 72 may include an end with a flange 72*a* disposed in base chamber 50, with flange 72*a* being larger than aperture 74. A washer 75 may be positioned on shaft 72 between flange 72*a* and base 24 adjacent to aperture 74.

A threaded bore 76 may extend in the end of shaft 72 along axis C and opening in chamber 50. Second force-applying element 68 in this example is a threaded rod 78. Rod 78 may be threadedly received in bore 76, and may extend from shaft 72 and into a threaded bore 80 in movable shank jaw 54. A retention pin 82 extends through a lateral bore 84 in shank jaw 54 and a lateral bore 86 in rod 78 to prevent the rod from rotating in bore 80. Shank jaw 54 may be moved toward and away from fixed shank jaw 52 by rotation of handle 70. Rotation of handle 70 rotates shaft 72 on rod 78, thereby moving shank jaw 54 along axis C, either toward the open position or the closed position, depending on the direction handle 70 is rotated.

Drive assembly 64 may further include a frame 88 for transferring force from shaft 72 to rail jaw 42 via the first force-applying element 66. Frame 88 includes a base section 88*a*. Shaft 72 extends through an aperture 89 in base section 88*a*. Washer 75 and flange 72*a* seat against a face of base section 88*a* of frame 88 facing shank jaw 54. Extending from outer, opposite edges of base section 88*a* of the frame are parallel arms 88*b* and 88*c* that extend through respective channels in shank jaw 54, such as channel 90 through which arm 88*c* extends, as shown particularly in FIG. 4. Frame arms 88*b* and 88*c* also extend through channel 56 in shank jaw 52. Channel 56 and channels in shank jaw 54, such as channel 90, allow the frame arms to move in a rectilinear direction parallel to shaft axis C and transverse to shank axis B. Shaft 72 extends through an aperture 91 in frame base section 88*a* with washer 75 disposed between flange 72*a* and base section 88*a*.

First force-applying element 66 is supported between distal ends of arms 88*b* and 88*c*. In this example, force-applying element 66 is a roller 92 mounted for rotating about a roller axis D that is parallel to jaw pivot axis A. Roller 92 contacts a contact surface 94*a* of a lever arm 94 extending generally radially from rail-jaw pivot axle 44. Contact surface 94*a* and lever arm 94, generally, are spaced circumferentially about jaw axis A from rail jaw 42.

Figure 8:
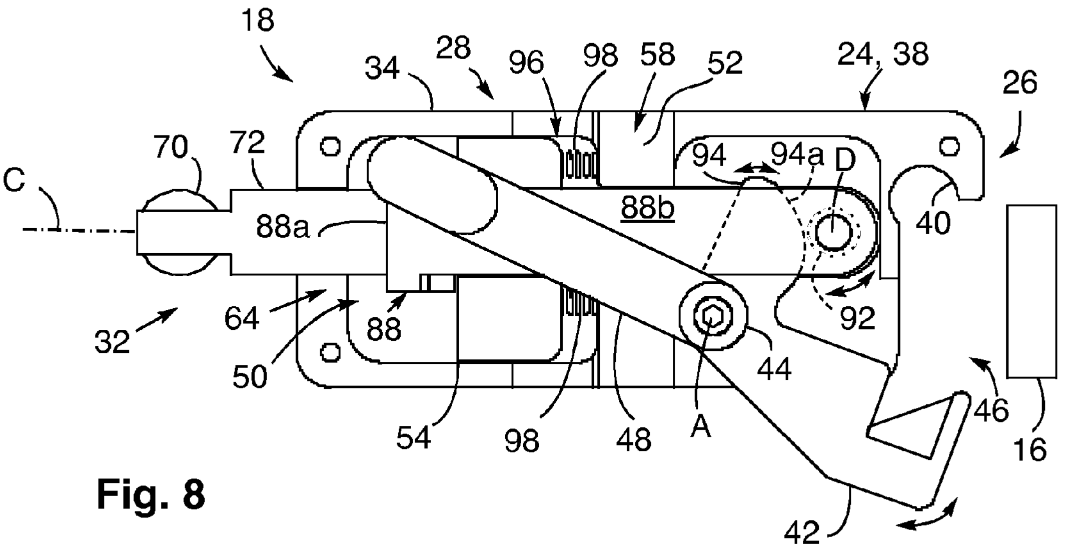
FIG. 8 is a side view of the base-clamp assembly of FIG. 2 with the near housing section removed.
Figure 9:
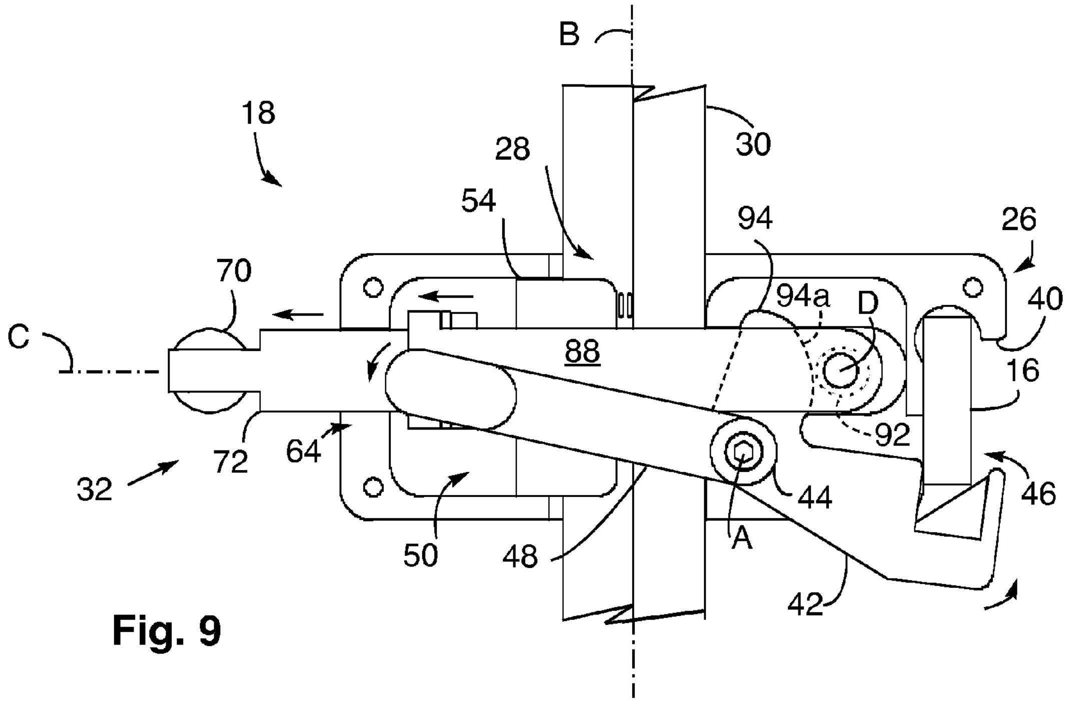
FIG. 9 is a side view of the base-clamp assembly of FIG. 2 with the near housing section removed, with a rail extending through a rail opening, and with an instrument-support shank extending through a shank opening.

As shown particularly in FIGS. 8 and 9, contact surface 94*a* is curved and contacts roller 92 at a location that is between frame arms 88*b* and 88*c*, which in this example is substantially normal to a direction of movement of the first force-applying element (roller 92) along shaft axis C at locations of contact of the first force-applying element on the contact surface during movement of rail jaw 42 between the open position shown in FIG. 8 and the closed position shown in FIG. 9. Roller 92 rolls against contact surface 94*a* as rail jaw 42 moves between the open and closed positions, producing little friction between the roller and lever arm 94. Rail jaw 42 is moved between the open and closed positions by movement of frame 88 along shaft axis C, which movement is caused by rotation of shaft 72 by handle 70.

Base clamp assembly 18 may include one or more bias elements 96 biasing shank jaw 54 toward the open position. In this example, the bias elements may act through shank jaw 54, rod 78, and the first and second force-applying elements to bias the movable rail jaw toward the closed position. The bias elements may be any structure that provides the bias noted. In this example, bias is provided by four compression springs 98 extending between movable shank jaw 54 and base 24. The springs urge shank jaw 54, and thereby rod 78 and frame base section 88*a*, away from shank jaw 52. As frame 88 moves along shaft axis C away from rail opening 46, roller 92 acts on jaw lever arm 94 to rotate rail jaw 42 about axis A counterclockwise or upwardly, as viewed in FIG. 8, toward the closed position.

Continuing to refer to FIG. 8, movement of release handle 48 upwardly causes rail jaw 42 to rotate clockwise or downwardly (as viewed in the figure) about pivot axis A, toward the open position. This also rotates lever arm 94 clockwise, causing frame 88 and roller 92 to move along axis C toward rail clamp 26. Frame base 88*a* accordingly moves shaft 72, rod 78 and shank jaw 54 in the same direction. This moves shank jaw 54 toward the closed position, but leaves sufficient room in shank opening 58 to receive freely a shank 30.

In use, then, base-clamp assembly 18 is positioned near to rail 16. As shown in dashed lines in FIG. 5, release handle 48 is lifted to open the rail jaw 42 so the base-clamp assembly 18 can be temporarily attached to any position along rail 16. As mentioned, upright movement of the release handle 48 rotates rail jaw 42 clockwise around axis A. This opens rail opening 46 for receiving rail 16. This also compresses springs 98 as frame 88 and shank jaw 54 move along axis C toward rail clamp 26.

When release handle 48 is released, springs 98 cause shank jaw 54 to move along axis C away from rail clamp 26. This also causes the main handle 70, shaft 72, threaded rod 78 and frame 88 to move away from rail clamp 26 along axis C. Roller 92 acting on jaw lever arm 94 pivots rail jaw 42 and release handle 48 counterclockwise around axis A, urging the rotating rail jaw 42 against rail 16. This temporarily keeps the base clamp assembly 18 attached to the rail and allows insertion of shank 30 through keyways 60 and 62 and shank opening 58.

After shank 30 of instrument-support apparatus 10 is inserted through shank opening 58, as shown in FIG. 6, main handle 70 may be turned to extend threaded rod 78 from shaft 72. Rod 78 is secured or fixed relative to shank jaw 54 by retention pin 82. Extension of rod 78 from shaft 72 thus moves shank jaw 54 toward the closed position and against shank 30. Shank 30 is pressed against fixed shank jaw 52, securing the shank to the base-clamp assembly, as shown in FIG. 7. This also moves shaft 72 away from shank clamp 28, moving frame 88 away from rail clamp 26. This causes roller 92 to pull against pivoting rail-jaw lever arm 94, thus tightening pivoting rail jaw 42 against rail 16, as shown in FIGS. 5 and 9. Securing of the base-clamp assembly to the rail and shank correspondingly secures instrument-support apparatus 10 to the rail. This two-step procedure facilitates attachment of an instrument 12 to rail 16 near to a patient position 14 on an operating table.

It is thus seen that a single action of tightening clamp-assembly handle 70 secures both the shank and the rail in the base clamp assembly. By loosening the handle 70, the shank can be moved up or down. In order to reposition the base along the rail, release handle 48 must also be raised to provide a slight amount of clearance between the rail and the rail jaws.

The above description is intended to be illustrative, and not restrictive. Many other embodiments will be apparent to those of skill in the art upon reviewing the above description. The scope of a disclosed invention should, therefore, be determined with reference to the appended claims, along with the full scope of equivalents to which such claims are entitled. Accordingly, while embodiments of a base-clamp assembly and methods of securing a shaft relative to a rail have been particularly shown and described, many variations may be made therein. This disclosure may include one or more independent or interdependent inventions directed to various combinations of features, functions, elements and/or properties, one or more of which may be defined in the following claims. Other combinations and sub-combinations of features, functions, elements and/or properties may be claimed later in this or a related application. Such variations, whether they are directed to different combinations or directed to the same combinations, whether different, broader, narrower or equal in scope, are also regarded as included within the subject matter of the present disclosure. An appreciation of the availability or significance of claims not presently claimed may not be presently realized. Accordingly, the foregoing embodiments are illustrative, and no single feature or element, or combination thereof, is essential to all possible combinations that may be claimed in this or a later application. Each claim defines an invention disclosed in the foregoing disclosure, but any one claim does not necessarily encompass all features or combinations that may be claimed.

Where the claims recite "a" or "a first" element or the equivalent thereof, such claims include one or more such elements, neither requiring nor excluding two or more such elements. Further, ordinal indicators, such as first, second or third, for identified elements are used to distinguish between the elements, and do not indicate a required or limited number of such elements, and do not indicate a particular position or order of such elements unless otherwise specifically stated.

The invention claimed is:

1. A base-clamp assembly for supporting an instrument-support apparatus having a shank extending adjacent to an equipment-mounting rail for supporting instruments relative to a patient position adjacent to the rail, the base-clamp assembly comprising:

a base;

a shank clamp for attaching the shank to the base;

a rail clamp having a first rail jaw fixedly supported relative to the base, and a second rail jaw mounted for pivoting relative to the base and opposing and movable relative to the first rail jaw, the first and second rail jaws forming a rail opening, the second rail jaw being movable between an open position in which the rail opening is sized for receiving a rail and a closed position in which the rail jaws securely hold the rail; and an actuator assembly operable for moving the second rail jaw relative to the first rail jaw, the actuator assembly including a first force-applying element movable relative to the base and the second rail jaw, for applying a first force to the second rail jaw tending to move the second rail jaw toward the closed position, and a drive assembly manipulable for moving the first force-applying element relative to the base, wherein the drive assembly includes a frame movable relative to the base and the first force-applying element includes a roller mounted to the frame for rotation about a roller axis, the roller applying the first force to the second rail jaw.

2. A base-clamp assembly for supporting an instrument-support apparatus having a shank extending adjacent to an equipment-mounting rail for supporting instruments relative to a patient position adjacent to the rail, the base-clamp assembly comprising:

a base;

a rail clamp having a first rail jaw fixedly positioned relative to the base, a second rail jaw opposing and movable relative to the first rail jaw, and a rail-jaw axle coupling the second rail jaw to the base for pivoting the second rail jaw relative to the base, the first and second rail jaws forming a rail opening, the second rail jaw being movable between an open position in which the rail opening is sized for receiving a rail and a closed position in which the rail jaws securely hold the rail;

a shank clamp having a first shank jaw fixedly positioned relative to the base and a second shank jaw opposing and movable relative to the first shank jaw, the first and second shank jaws forming a shank opening, and the second shank jaw being movable between an open position in which the shank opening is sized for receiving a shank of the instrument-support apparatus and a closed position in which the shank jaws securely hold the shank;

an actuator assembly operable for moving the second rail jaw relative to the first rail jaw and moving the second shank jaw relative to the first shank jaw, the actuator assembly including a first force-applying element movable relative to the base and the second rail jaw for applying a first force to the second rail jaw tending to close the second rail jaw, a second force-applying element for applying a second force to the second shank jaw tending to move the second shank jaw between the open and closed positions, and a drive assembly for moving the first force-applying element relative to the second force-applying element; and at least one bias element biasing the second shank jaw toward the open position, and the at least one bias element, acting through the second shank jaw and the first and second force-applying elements to bias the second rail jaw toward the closed position.

* * * * *